United States Patent
Nakamura

(10) Patent No.: US 6,994,778 B2
(45) Date of Patent: Feb. 7, 2006

(54) MICROFLUIDIC DEVICE AND ANALYZING METHOD USING THE SAME

(75) Inventor: Shin Nakamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 212 days.

(21) Appl. No.: 10/673,470

(22) Filed: Sep. 30, 2003

(65) Prior Publication Data
US 2004/0089547 A1    May 13, 2004

(30) Foreign Application Priority Data
Nov. 11, 2002  (JP) ............................. 2002-327065

(51) Int. Cl.
*G01N 27/447*  (2006.01)
*G01N 27/453*  (2006.01)
*B01L 3/02*    (2006.01)

(52) U.S. Cl. ...................... 204/453; 204/604; 422/100

(58) Field of Classification Search .................. 422/70, 422/100, 103; 204/601, 604, 451, 453
See application file for complete search history.

(56) References Cited

FOREIGN PATENT DOCUMENTS

WO       WO-00/54041 A1 *   9/2000

* cited by examiner

*Primary Examiner*—Alex Noguerola
(74) *Attorney, Agent, or Firm*—Manabu Kanesaka

(57) ABSTRACT

A microfluidic device includes a base member, a separating channel, and a sample quantity control channel branching from the separating channel. The separating channel has one end projecting from the base member, and the one end forms a sample introduction portion. The other end of the separating channel and a forward end of the sample quantity control channel have opening and closing mechanisms, respectively. A capacity of the sample quantity control channel corresponds to a sample quantity to be injected.

10 Claims, 3 Drawing Sheets

MICROFLUIDIC DEVICE AND ANALYZING METHOD USING THE SAME

BACKGROUND OF THE INVENTION AND RELATED ART STATEMENT

The invention relates to a microfluidic device of an electrophoretic apparatus for analyzing a small quantity of a sample at a high speed with a high resolution, and an electrophoretic analyzing method using the same.

An electrophoretic analysis using a microfluidic device has been widely used in a field of biochemistry, molecular biology, clinical medical, and analysis of deoxyribonucleic acids (hereinafter simply referred to "DNA") and proteins.

When a small quantity of DNA, protein or the like is analyzed, an electrophoresis has been conventionally used. As an example of a device, there has been known a capillary electrophoretic apparatus. In the capillary electrophoretic apparatus, a migration buffer is filled in a glass capillary (hereinafter referred to simply "capillary") having an inner diameter of less than 100 $\mu$m. After a sample is injected into one end of the capillary, a high voltage is applied between both ends thereof so that a substance to be analyzed travels in the capillary. The interior of the capillary has a large surface area relative to a capacity, i.e. a high cooling effect. Therefore, it is possible to apply a high voltage, so that a small quantity of a sample such as DNA can be analyzed at a high speed with a high resolution.

Recently, instead of the capillary whose handling is troublesome, as a device with a high analyzing speed and a small size, there has been proposed a microfluidic device, i.e. electrophoretic chip device, formed of joined two base plates, as disclosed in D. J. Harrison et al., Science 261 (1993) pp. 895–897, and Anal. Chem. Acta 283 (1993) pp. 361–366.

An example of the microfluidic device is shown in FIGS. 4(A)–4(C). The microfluidic device is formed of a pair of transparent base plates 1 and 2 generally made of glass, quartz, resin or the like. A loading channel 4 and a separating channel 5, which cross each other, are formed in one base member 2, as shown in FIG. 4(B). Reservoirs 3 are formed in the other base member 1 as a through-hole at positions corresponding to respective both ends of the loading channel 4 and the separation channel 5, as shown in FIG. 4(A). The base plates 1 and 2 are laminated and joined together, as shown in FIG. 4(C). In the conventional microfluidic device described above, the sample is basically injected into the channel with a cross injector design formed of the loading channel 4 and the separating channel 5 crossing each other.

When such a microfluidic device is used, a migration buffer is injected into the loading channel 4 and the separation channel 5 from any one of the reservoirs 3. Then, about 1–2 $\mu$l (micro liter) of a sample is injected into the reservoir 3 located at one end of the loading channel 4. A predetermined voltage is applied to plural portions by pinching or the like through electrodes inserted into the respective reservoirs 3 or electrodes provided to the respective reservoirs 3 in advance, so that the sample travels uniformly in the loading channel 4 in an electrophoretic manner without going into the separating channel 5 from a crossing point 6. Accordingly, the sample is guided to the crossing point 6 of the loading channel 4 and the separating channel 5.

Next, the applied voltage is switched to the separating channel 5. Also, the voltage is applied to the loading channel 4 so that the sample is moved in a reverse direction from the crossing point 6. Accordingly, only the sample at the crossing point 6 is introduced into the separating channel 5 to carry out the electrophoretic separation. A detector is disposed at a suitable position of the separating channel 5 for detecting a separated component.

As described above, only the sample present at the crossing point 6 is introduced into and separated at the separating channel 5. An actual volume of the sample for the analysis is only from several pico-liters (hereinafter referred to "pl") to several hundreds pl. However, it is necessary to inject several $\mu$l of the sample into the microfluidic device. Therefore, a large quantity of the sample is not used for the analysis. The microfluidic device described above is sometimes used for analyzing a very expensive sample. Therefore, if the analysis requires only a small quantity of a sample, it is possible to reduce the running cost. Thus, there has been a strong demand for reducing a quantity of a sample.

In view of the above problems, the present invention has been made, and an object of the invention is to provide a microfluidic device having a structure in which it is possible to prevent an unnecessary sample from being injected.

Further objects and advantages of the invention will be apparent from the following description of the invention.

SUMMARY OF THE INVENTION

According to the present invention, a microfluidic device includes a base member, a separating channel, and a sample quantity control channel branching from the separating channel. The separating channel has one end extending in a direction to project from the base member, and the one end has an opening at a forward end thereof to be a sample introduction portion. The other end of the separating channel and a forward end of the sample quantity control channel have opening and closing mechanisms, respectively. A capacity of the sample quantity control channel corresponds to a sample quantity to be injected.

A sample quantity in a pl level to be injected into the separating channel is controlled by the capacity of the sample quantity control channel, so that only the controlled sample quantity is injected into the separating channel through the sample injecting portion.

The sample injecting portion is provided at a lower surface of the base member. The other end of the separating channel and the forward end of the sample quantity control channel include openings, respectively. The closing mechanism is provided at the opening, respectively. As an example of the opening and closing mechanism, a valve may be employed.

According to the present invention, an analyzing method using the microfluidic device includes the steps of injecting a migration buffer into the microfluidic device; injecting a sample in a quantity corresponding to a capacity of a sample quantity control channel; and applying a voltage between a sample injecting portion and one end of the separating channel to thereby carry out electrophoresis to separate the injected sample.

BRIEF DESCRIPTION OF THE DRAWINGS

FIGS. 2(A) and 2(B) are plan views showing a method of introducing a sample in the microfluidic device of the invention, wherein FIG. 2(A) shows a process of injecting a migration buffer, and FIG. 2(B) shows a process of introducing the sample;

FIGS. 4(A)–4(C) are views showing a conventional microfluidic device, wherein FIG. 4(A) is a plan view showing one of base plates, FIG. 4(B) is a plan view showing the other of the base plates, and FIG. 4(C) is a side view showing a state where both base plates are laminated and joined.

DETAILED DESCRIPTION OF PREFERRED EMBODIMENT

Figure 1:
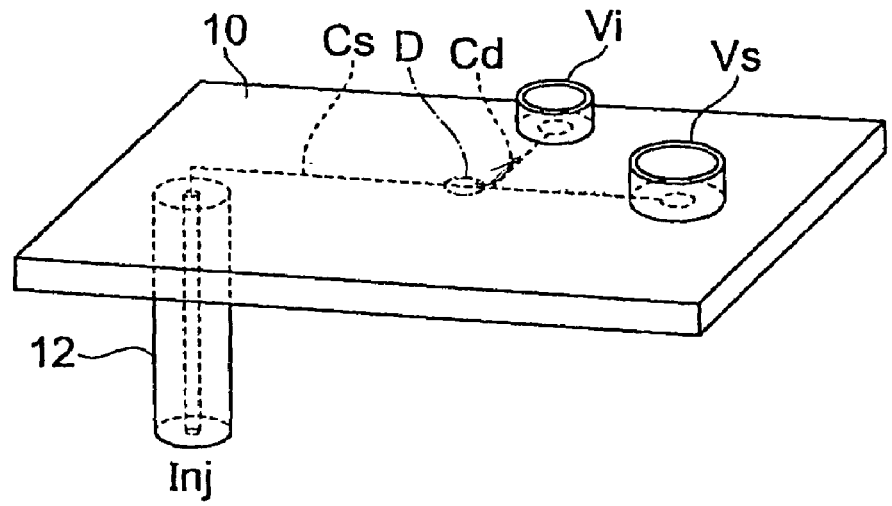
FIG. 1 is a perspective view showing a microfluidic device according to an embodiment of the present invention.

Hereunder, embodiments of the invention will be explained with reference to the accompanying drawings. FIG. 1 is a perspective view showing a microfluidic device of an embodiment according to the present invention.

A channel is formed in one of a pair of transparent base plates made of glass, quart, resin or the like, and both base plates are joined to thereby obtain a base member 10. A separation channel Cs and a sample quantity control channel Cd branching from the separating channel Cs are formed in the base member 10. The separating channel Cs has one end with an opening at a lower surface side of the base member 10 (left side in the drawing). A cylindrical member 12 is connected to the opening so that the separating channel Cs extends to the lower surface side of the base member 10. A forward end of the cylindrical member 12 constitutes a sample injecting portion Inj.

The other end of the separating channel Cs includes an opening at an upper surface side of the base member 10, and a valve Vs as an opening and closing mechanism is disposed at the opening. A detecting portion D is situated at a side of the other end of the separating channel Cs, and the sample quantity control channel Cd branches from the separating channel Cs between the detecting portion D and the valve Vs. A forward end of the sample quantity control channel Cd is also provided with an opening at an upper surface side of the base member 10, and a valve Vi as an opening and closing mechanism is provided at the opening.

The separating channel Cs formed in the base member 10 has a width of 10–200 $\mu$m, a depth of 2–90 $\mu$m, and a length of 10–100 mm. The cylindrical member 12 has a cylindrical shape with a hole having a diameter of 500–5,000 $\mu$m. A capacity of the sample quantity control channel Cd is designed to be a sample quantity actually injected into the separating channel Cs. The valves Vi and Vs have structures of diaphragms, respectively.

Figure 2A:
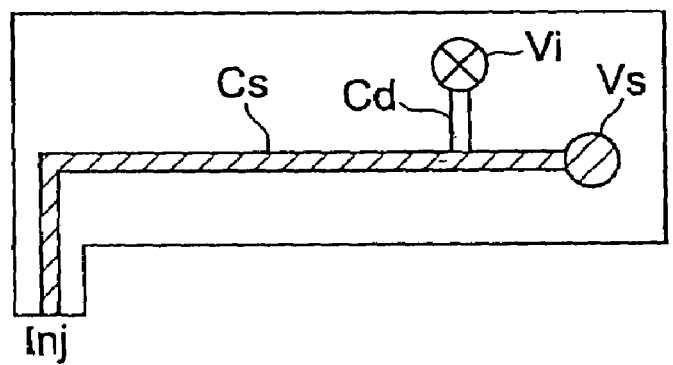
Figure 2B:
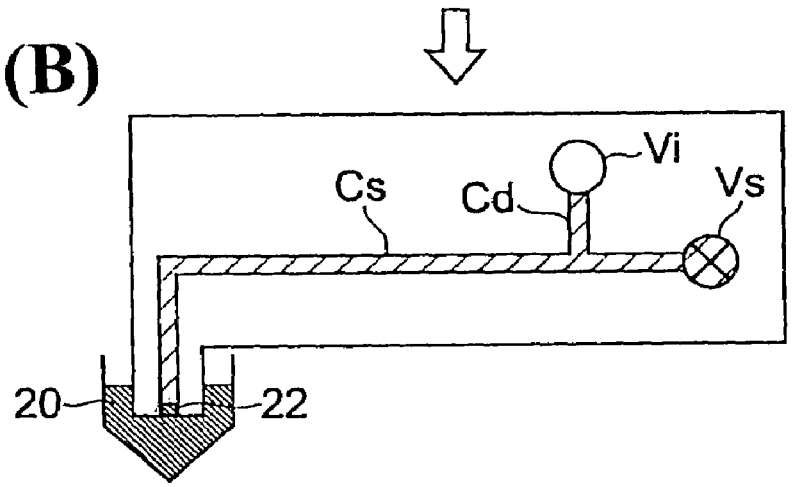
Figure 3:
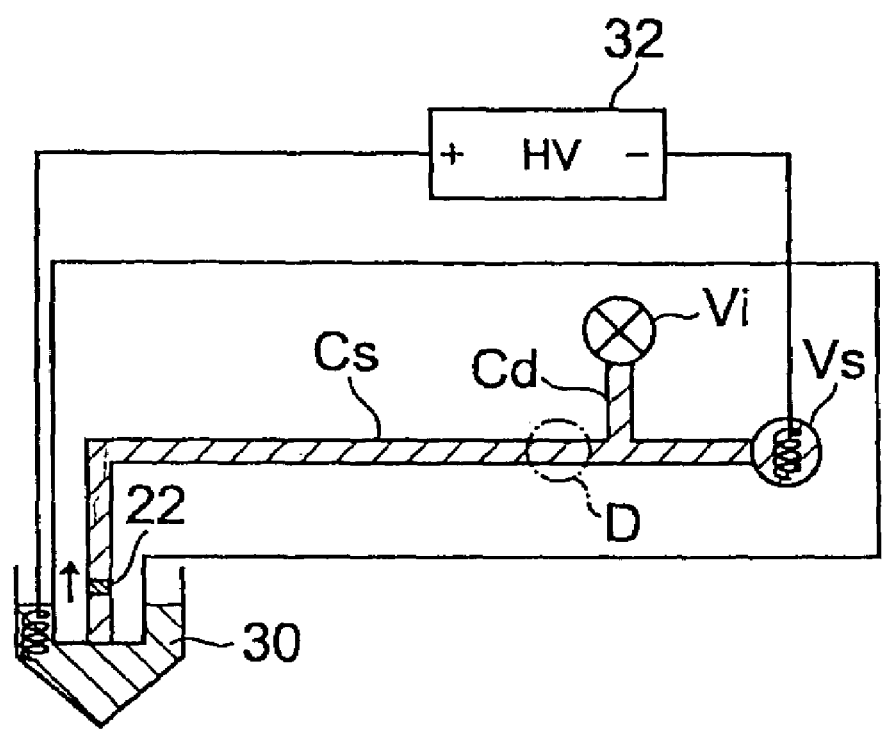
FIG. 3 is a plan view showing an electrophoretic separation process in the microfluidic device of the invention.
Figure 4A:
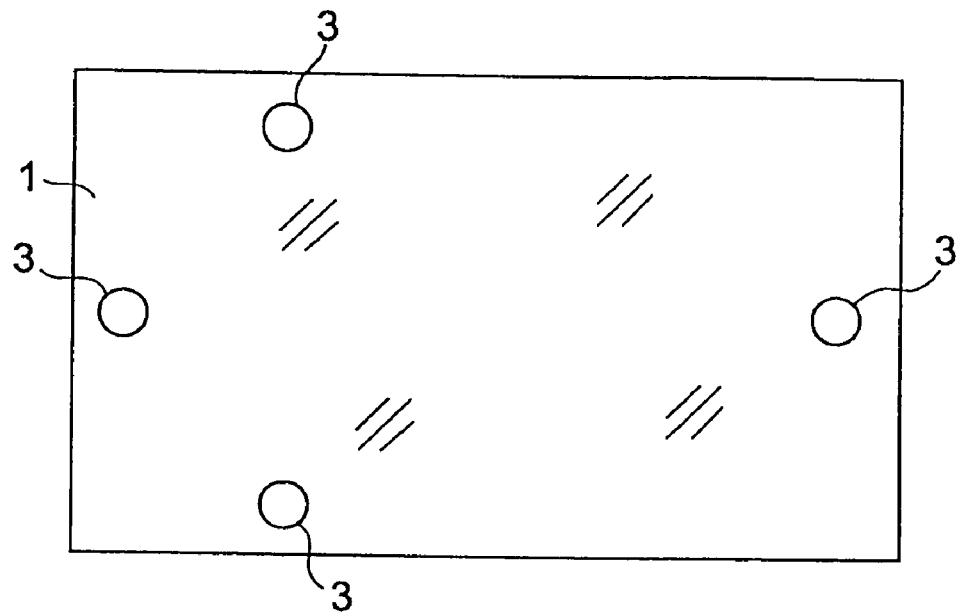
Figure 4B:
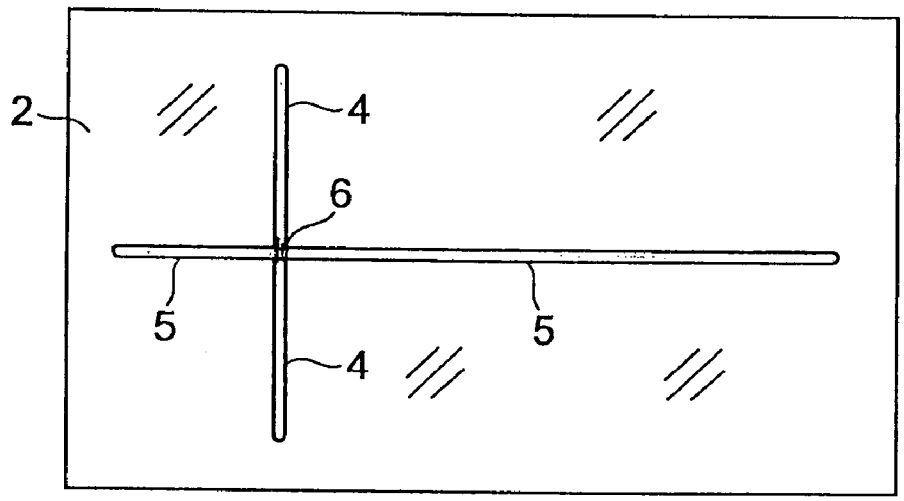
Figure 4C:
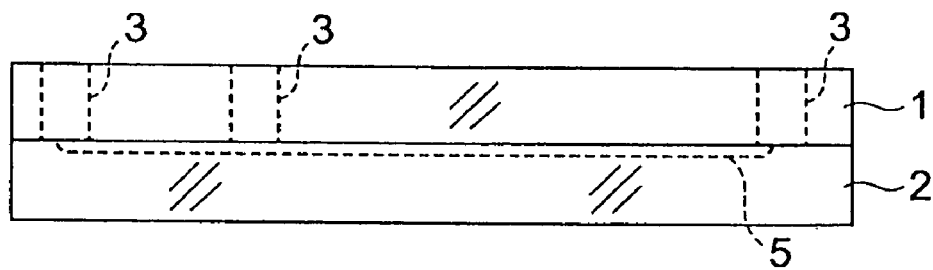

An analyzing method using the microfluidic device according to the present embodiment will be explained with reference to FIGS. 2(A), 2(B) and 3. In FIGS. 2(A), 2(B) and 3, the microfluidic device is shown schematically.

As shown in FIG. 2(A), the valve Vs is opened in a state that the valve Vi is closed, and a migration buffer is injected through a port of the valve Vs. The migration buffer may be injected from the valve Vs side under pressure, or from the sample introduction portion Inj under a negative pressure or drawing pressure. Since the valve Vi is closed, the migration buffer is not introduced into the channel Cd.

After the migration buffer is injected into the separating channel Cs, as shown in FIG. 2(B), the valve Vs is closed. Then, the sample introduction portion Inj is immersed into a sample 20, and the valve Vi is opened. At this time, the migration buffer in the separating channel Cs is introduced into the channel Cd by the capillary phenomenon. Accordingly, the sample 20 is introduced into the separating channel Cs through the sample injecting portion Inj by a volume corresponding to a volume of the migration buffer introduced into the channel Cd.

When the valve Vi has a tightly sealed structure, the migration buffer in the separating channel Cs is also introduced into the channel Cd by a volume change corresponding to the capacity of the channel when the valve Vi is opened. Reference numeral 22 represents a sample introduced into the separating channel Cs.

After the sample is introduced, as shown in FIG. 3, the valve Vi is closed again. Then, the sample injecting portion Inj is immersed in a reservoir of the migration buffer 30 so that the migration buffer is filled in both ends of the separating channel Cs, and the valve Vs is opened. Since the migration buffer is already injected in the separating channel Cs, both ends of the separating channel Cs are filled with the migration buffer.

Next, electrodes are inserted into the migration buffer at the both ends of the separating channel Cs, respectively, and a voltage from a high voltage power supply 32 is applied between the both ends of the separating channel Cs to thereby carry out an electrophoretic separation.

A separation peak can be detected at the detecting position D with various methods such as, for example, an optical fluorescent detecting method, an ultraviolet light (UV) absorption detecting method, a chemical luminescence detecting method, and an electrochemical detecting method including a working electrode and a sensing electrode. It is also possible to ionize the sample at the end of the separating channel Cs with an electrospray method, thereby detecting with a mass spectrometer.

After completion of the analysis, the valves Vi, Vs are opened, and the migration buffer is flushed with a pressure from the end of the channel Cd. If further cleaning is necessary, the migration buffer is injected and flushed again in the same way.

According to the present invention, the microfluidic device includes the sample quantity control channel branched from the separating channel. The capacity of the sample quantity control channel is the same as the quantity of the sample to be introduced. That is, the capacity of the sample quantity control channel defines the quantity of the sample required for the separation. Therefore, it is possible to directly introduce a very small quantity of the sample into the end portion of the separating channel.

In the microfluidic device of the invention, it is not necessary to apply a voltage in a complicated manner. Further, suction or compression pump is not required. In the microfluidic device of the invention, a volume change in a sealed space is utilized, thereby making the method of introducing the sample very simple. Also, it is not necessary to perform the electrophoresis for introducing the sample. Therefore, there is no influence of an ionic strength of the sample and ionic foreign substances in the sample.

While the invention has been explained with reference to the specific embodiments of the invention, the explanation is illustrative and the invention is limited only by the appended claims.

What is claimed is:

1. A microfluidic device for analyzing a sample, comprising:
   a base member;
   a separating channel formed in the base member;
   a sample injecting portion formed at one end of the separating channel;
   a sample quantity control channel formed in the base member and branching from the separating channel, said sample quantity control channel having a volume for the sample to be introduced from the sample injecting portion;

a first opening and closing mechanism disposed at the other end of the separating channel, said first opening and closing mechanism being opened when a migration buffer is introduced into the separating channel, and then closed; and a second opening and closing mechanism disposed at one end of the sample quantity control channel away from the separating channel, said second opening and closing mechanism being closed when the migration buffer is introduced into the separating channel, and opened when the sample injecting portion is immersed into a sample so that the sample is introduced into the separating channel for the volume of the sample quantity control channel while the migration buffer in the separating channel enters the sample quantity control channel by capillary phenomenon.

2. A microfluidic device as claimed in claim 1, further comprising a projection projecting from the base member to communicate with the separating channel, and having a distal end forming the sample injecting portion.

3. A microfluidic device as claimed in claim 2, wherein said base member includes a lower surface from which said projection projects, and an upper surface having an opening for the other end of the separating channel and an opening for the one end of the sample quantity control channel, said first and second opening and closing mechanisms being disposed in the respective openings.

4. A microfluidic device as claimed in claim 1, wherein said first and second opening and closing mechanisms are valves.

5. A microfluidic device as claimed in claim 1, wherein said base member is formed of first and second plates laminated together.

6. A microfluidic device as claimed in claim 1, further comprising means for holding the sample, to be connected to the sample injecting portion when the sample is introduced into the separating channel, and means for holding the migration buffer, to be connected to the sample injecting portion when the sample is separated by electrophoresis.

7. An analyzing method for analyzing a sample, comprising the steps of:

filling a migration buffer in a separating channel while a sample quantity control channel branching from the separating channel is empty without filling the migration buffer;

introducing the sample into the separating channel from a sample injecting portion of the separating channel for an amount corresponding to a volume of the sample quantity control channel while the migration buffer in the separating channel is introduced into the sample quantity control channel by capillary phenomenon; and applying a voltage between the sample injecting portion and an end of the separating channel away from the sample injecting portion so that the sample is separated by electrophoresis.

8. An analyzing method as claimed in claim 7, wherein said step of filling the migration buffer is performed by opening a first opening and closing mechanism formed at an end of the separating channel away from the sample injecting portion, and closing a second opening and closing mechanism at the sample quantity control channel located away from the separating channel; and said step of introducing the sample is performed by immersing the sample injecting portion in the sample, and opening the second opening and closing mechanism while the first opening and closing mechanism is closed; after closing the second opening and closing mechanism, the step of applying the voltage is performed.

9. An analyzing method as claimed in claim 8, further comprising the step of immersing the sample injecting portion in the migration buffer after the step of introducing the sample and before the step of applying the voltage.

10. A microfluidic device for analyzing a sample, comprising:

a base member;

a separating channel formed in the base member;

a sample injecting portion formed at one end of the separating channel;

a sample quantity control channel formed in the base member and branching from the separating channel, said sample quantity control channel having a volume for the sample to be introduced;

a first opening and closing mechanism disposed at the other end of the separating channel;

a second opening and closing mechanism disposed at one end of the sample quantity control channel away from the separating channel; and a projection projecting from the base member to communicate with the separating channel, and having a distal end forming the sample injecting portion;

wherein said base member includes a lower surface from which said projection projects, and an upper surface having an opening for the other end of the separating channel and an opening for the one end of the sample quantity control channel, said first and second opening and closing mechanisms being disposed in the respective openings.

* * * * *